United States Patent [19]

Adair

[11] 4,417,710
[45] Nov. 29, 1983

[54] COMBINED SURGICAL INSTRUMENT AND TUBE HOLDER DEVICE

[75] Inventor: Edwin L. Adair, Denver, Colo.

[73] Assignee: The Urology Group, P.C., Littleton, Colo.

[21] Appl. No.: 342,209

[22] Filed: Jan. 25, 1982

[51] Int. Cl.³ .............................................. F16L 3/00
[52] U.S. Cl. .................................. 248/51; 248/205 A
[58] Field of Search ............... 604/174, 175, 176, 177, 604/178, 179, 180; 128/DIG. 26; 248/51, 52, 205 A, 68 R, 74 PB, 213.4; 24/204, 206

[56] References Cited

U.S. PATENT DOCUMENTS

| | | | |
|---|---|---|---|
| 3,128,072 | 4/1964 | Shibata | 248/205 A |
| 3,146,778 | 9/1964 | Krawiec | 248/205 A |
| 3,321,068 | 5/1967 | Beach | 248/205 A |
| 3,387,341 | 6/1968 | Mates et al. | 248/205 R |
| 3,677,250 | 7/1972 | Thomas | 128/DIG. 26 |
| 3,826,254 | 7/1974 | Mellor | 604/180 |
| 3,834,380 | 9/1974 | Boyd | 128/DIG. 26 |
| 4,074,397 | 2/1978 | Rosin | 24/306 |

FOREIGN PATENT DOCUMENTS 668051  3/1952  United Kingdom ....... 248/DIG. 14

*Primary Examiner*—William H. Schultz
*Assistant Examiner*—Ramon O. Ramirez
*Attorney, Agent, or Firm*—Fields, Lewis, Pittenger & Rost

[57] ABSTRACT

A device is provided for yieldably supporting a tube and/or cord extending from a surgical instrument. The device includes a pad which is adhesively securable to a surgical drape or other surface and is connected to a releasable tube holding means by a stretchable member. The tube holding means includes a strip having a foam layer on one side and a fabric layer of intertwining material on the other side and a tab attached to one end of the strip and having an interlocking surface which releasably adheres to the fabric layer so as to hold the tube and/or cord in desired location while allowing them to move in response to movement of the surgical instrument. In one embodiment, the outer side of the pad has a layer of intertwining material and a strip of interlacing material is adhesively attached to the surgical instrument so that the instrument can be nested on the pad by pressing the interlacing material against the intertwining material on the pad.

10 Claims, 6 Drawing Figures

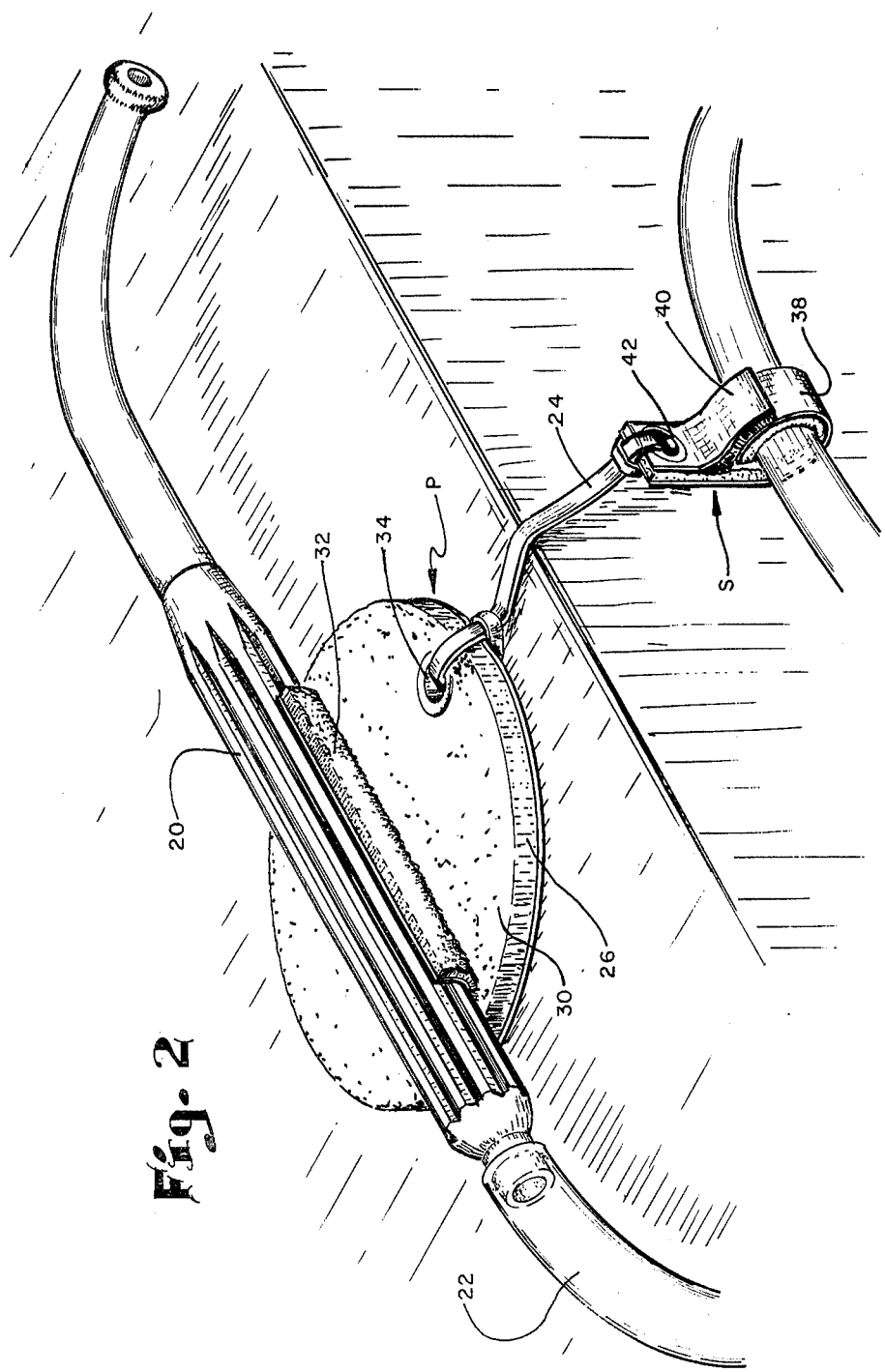

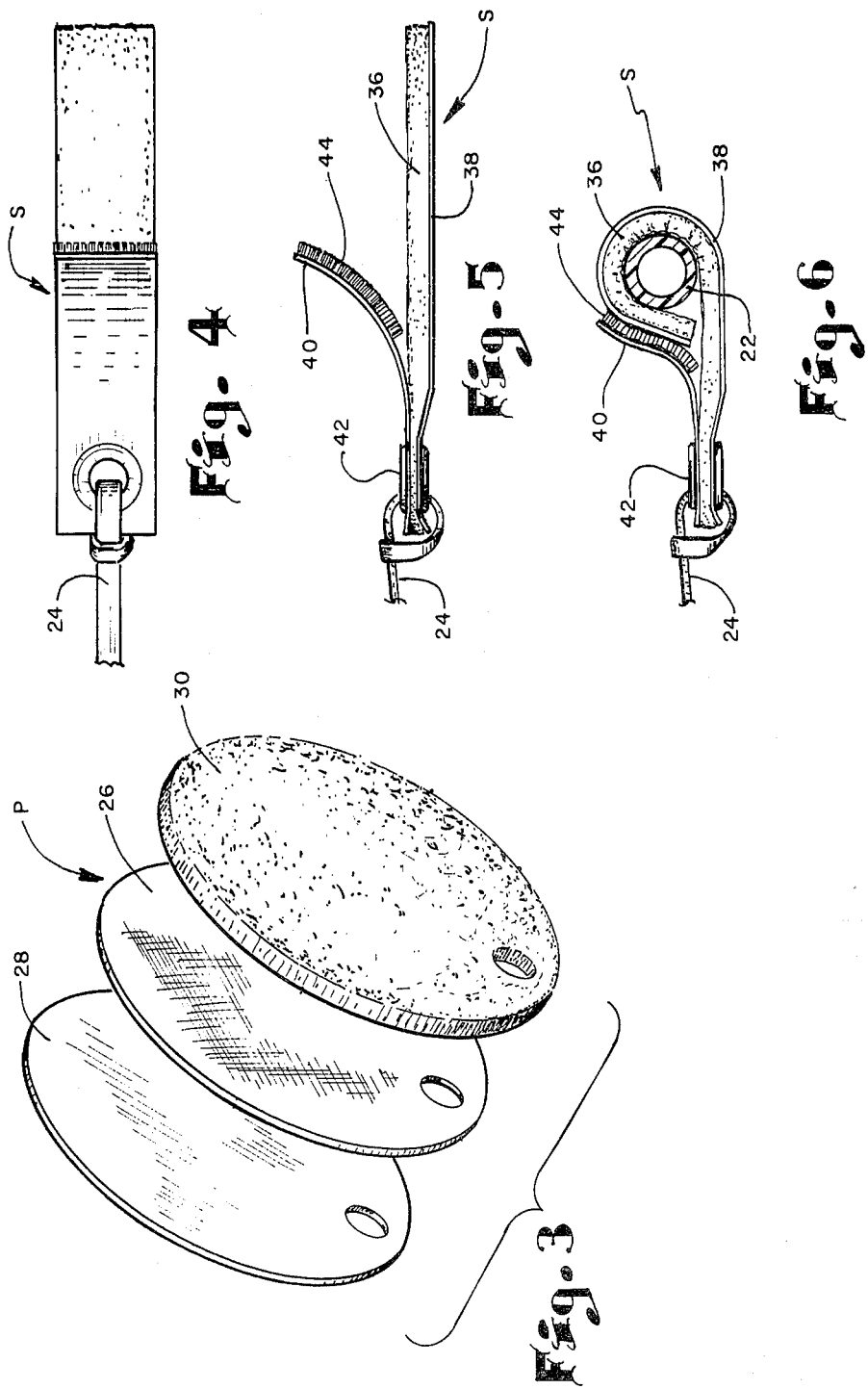

4,417,710

COMBINED SURGICAL INSTRUMENT AND TUBE HOLDER DEVICE

TECHNICAL FIELD

This invention relates to a surgical instrument holder, and more particularly to a holder which has the dual function of providing a nesting place for the surgical instrument when not in use and for yieldably holding the tube or cord attached to the instrument in a predetermined location but permitting some movement in response to manipulation of the surgical instrument so as not to unduly restrain movement thereof.

BACKGROUND ART

Tube and cord holding devices of various types are well known in the prior art. For example, U.S. Pat. No. 3,677,250 to Thomas for "Tabbed Anchoring Tape Means" discloses a pair of spaced anchoring pads interconnected by a strap which is adapted to be wrapped around a cord. The pads are each adhesively connected to a supporting surface. This structure has the advantage of holding a tube securely in a predetermined location but permits almost no movement of the tube and therefore is not satisfactory for use at a location close to the surgical device or other instrument which is connected to the tube which must be moved around or manipulated by the user.

Another tube holder is shown in U.S. Pat. No. 4,074,397 to Rosen for "Device for Securing Cords, Tubes, and the Like". This tube holder includes a pad which is adhesively secured to a supporting surface and has a fabric surface on the other side. A tab is cut from a portion of the pad and has an interlacing surface on the end thereof such as "Velcro" so that the tab can be wrapped around the cord and the interlacing means on the end of the tap engaged with the intertwining fabric surface of the pad. Like Thomas, this device will hold a cord very securely but does not allow movement of the cord upon manipulation of the device to which the cord is attached.

Another tube holder is shown in U.S. Pat. No. 3,782,388 to Page for "Medical Tube Holder" wherein a stretchable cord is connected to a pad which is adhesively adhered to a human body. The other end of the stretchable cord has an annular clip portion which is removably attached to a cord and allows some movement of the cord on the patient as the patient moves. However, there is no teaching of providing a nesting place on the pad for a surgical instrument when not in use.

DISCLOSURE OF THE INVENTION

In accordance with this invention a device is provided for releasably supporting a surgical instrument and a tube or wire connected thereto. This device comprises an attachment pad having an adhesive coating on a first side thereof for securing the pad to a permanent fixture. A tube-holding strip having a resilient foam layer on one side and a fabric layer of intertwining material on the other side has a tab attached adjacent one end thereof. This tab extends coextensively with at least a portion of the foam layer side and has interlacing means on the side facing the foam layer so that when the foam layer is looped around a tube or wire the tab overlaps the fabric side of the strip whereupon the interlacing means is engagable with the intertwining materials to releasably hold the tube and wire. The device additionally includes a resilient connecting strap having one end connected to the attachment pad and the other end connected to the tube-holding strip so that the tube or wire is held in a predetermined place but is yieldably movable in response to manipulation of the surgical instrument so as not to restrain movement of the instrument.

In one embodiment, the attachment pad has an intertwining surface on the opposite side from the adhesive surface and an attachment strip having an adhesive coating on one side is attached to a surgical instrument and has a surface of interlacing material on the other side for engagement with the intertwining surface of the pad to provide a nesting place for the instrument when it is not in use.

With this invention, a simple yet highly useful and novel device is provided which will hold surgical instrument tubes or cords in a relatively fixed position, but allows some yielding due to the resiliency of the connecting strap so that the surgical instrument can be easily manipulated. Furthermore, the attachment pad can provide the dual function of anchoring one end of the resilient connecting strap and of providing a nesting place for the tool when not in use.

It will be understood as used herein that wherever the word "tube" is used that it is intended to include an electrical conduit or wire and wherever the term "surgical instrument" is used it is intended to include any medical device which must be manipulated or adjusted in use and has wires or tubes attached to it.

Other advantages of this invention will become apparent from the description which follows, taken in conjunction with the accompanying drawings.

BRIEF DESCRIPTION OF THE DRAWINGS

FIG. 2 is an enlarged perspective view showing the use of the attachment pad as a nesting place for a surgical instrument;

FIG. 3 is an exploded perspective view of the pad of FIG. 2 showing the details of the construction thereof;

FIG. 4 is a top plan view of the tube-holding strip shown in FIGS. 1 and 2;

FIG. 5 is a side elevation of the tube-holding strap of FIG. 4; and

FIG. 6 is a side elevation, of the tube-holding strap of FIG. 5, but showing a tube in place.

DESCRIPTION OF THE PREFERRED EMBODIMENTS

Figure 1:
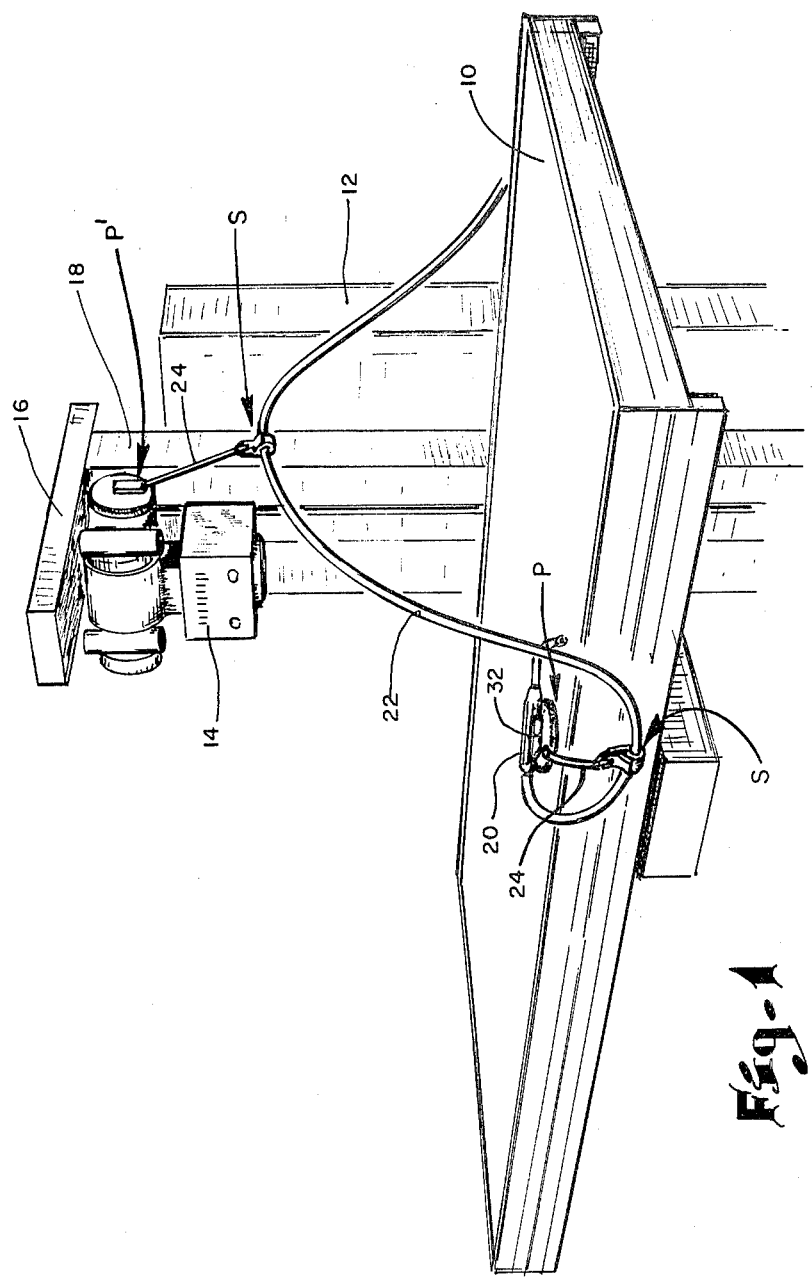
FIG. 1 is a perspective view of a patient operating table or an examination table showing two forms of the tube holder of this invention.

In accordance with this invention, a device for releasably supporting a surgical instrument and a tube or wire connected thereto is provided. As best seen in FIGS. 1 and 2, the device can be used with an examination or operating table 10. The table is adjustable up and down on a support 12 and is provided with an x-ray unit 14 supported over the table from an arm 16 attached to a column 18.

A surgical instrument or other medical operative device 20 is connected to a hose 22 and is manipulated by the doctor or nurse as required during a surgical or operative procedure. Conveniently, one supporting device is attached to the upper surface of the table or surgical drape by means of pad P which is interconnected with a tube-holding strip S by means of a resilient strap 24. A second holding device has a pad P' attached to a surface of x-ray unit 14 and is interconnected by a resilient strap 24 with tube-holding strip S, all as seen in FIG. 1. It will be understood that the holding device could hold electrical wires as well as tubes and various types of surgical devices or instruments can be used other than the irrigation device illustrated.

As can best be seen in FIG. 3, pad P comprises a fabric layer 26 having an adhesive surface on one side thereof for adhesively applying the pad to the table or surgical drape. Conveniently, layer 26 is protected by a removeable cover 28 prior to use. The other side of fabric layer 26 is permanently attached to a nesting surface 30 having a relatively loosely woven intertwining material thereon. Conveniently, instrument 20 has an attachment strip 32 adhesively attached thereto and having a surface of interlacing material with a plurality of small hooks, such as "Velcro" which releasably interlocks with the intertwining surface of the pad to provide a nesting place for the instrument when not in use.

Pad P also is provided with an eyelet 34 through which a resilient strap 24 is attached as shown. This strap may be made of any resilient material but in practice a rubberband has been found to be entirely satisfactory.

Conveniently, the other end of strap 24 is connected to holding-strip S whose structure can best be seen in FIGS. 2, 4, 5 and 6. Strip S includes a length of foam material 36 conveniently attached to a layer of supporting material 38, such as a piece of fabric. A tab comprising a second strip of fabric 40 is connected to one end of the foam material, as by an eyelet 42, the other end of strip 40 being provided with a layer of interlacing material 44, such as "Velcro". As best seen in FIGS. 2 and 6, the foam material 36 can be wrapped around tube 22 and interlacing material 44 on the tab 40 brought into contact with the fabric supporting material surface 38 to hold the tube in place. Thus, the holding device shown serves a dual purpose of providing a nesting or holding place for the instrument when not in place on top of the pad and also provides a resilient holding means for the tube providing some movement for the tube when the instrument is being manipulated by the user. A second embodiment as shown in FIG. 1 wherein pad P' is of generally rectangular configuration, although the particular shape is unimportant, which is attached to the x-ray unit and supports a tube but does not serve as a nesting place for a surgical instrument.

From the foregoing, the advantages of this invention are readily apparent. A surgical instrument and tube-holding device has been provided which has the function in one embodiment of releasably holding a tube in a relatively fixed position but allowing it to be moved in response to manipulation of the instrument by the user. Another embodiment, the device provides a dual function of not only holding a tube but also providing a nesting place for the instrument when it is not in use.

The invention has been described in detail with particular reference to preferred embodiments thereof, but it will be understood that variations and modifications can be effected within the spirit and scope of the invention.

I claim:

1. A device for releasably supporting a surgical instrument and a tube or wire connected thereto, said device comprising:

an attachment pad having an adhesive coating on a first side thereof for securing said pad to a permanent fixture;

a tube holding strip having a resilient foam layer on one side and a fabric layer of intertwining material on the opposite side;

a tab attached to said strip adjacent one end thereof and extending coextensively with at least a portion of said foam layer side, said tab having interlacing means on the side thereof facing said foam layer so that when said foam layer is looped around a tube or wire said tab overlaps the fabric side of said strip whereupon said interlacing means is engagable with said intertwining material to releasably hold the tube or wire; and a resilient connecting strap having one end connected to said attachment pad and the other end connected to said tube holding strip so that the tube or wire is held in a predetermined place but is yieldably movable in response to manipulation of the surgical instrument so as not to restrain movement of the instrument.

2. A device, as claimed in claim 1, further including:
a first eyelet in said pad; and
a second eyelet in said one end of said strip said one end of said connecting strap being connected to said first eyelet and said other end of said strap being connected to said second eyelet.

3. A device, as claimed in claim 2, wherein:
said first eyelet is adjacent the edge of said pad.

4. A device, as claimed in claim 2, wherein:
said second eyelet attaches said tab to said strip.

5. A device, as claimed in claim 1, wherein:
said strap is a rubber band.

6. A device for releasably supporting a surgical instrument and a tube or wire connected thereto, said device comprising:

an attachment pad having an adhesive coating on a first side thereof for securing said pad to a surgical drape, and an intertwining surface on the opposite second side;

a tube holding strip having a resilient foam layer on one side and a fabric layer of intertwining material on the opposite side;

a tab attached to said strip adjacent one end thereof and extending coextensive with at least a portion of said foam layer side, said tab having interlacing means on the side thereof facing said foam layer so that when said foam layer is looped around a tube or wire said tab overlaps the fabric side of said strip so that said interlacing means is engagable with said intertwining material to releasably hold said tube or wire;

a resilient connecting strap having one end connected to said attachment pad and the other end connected to said tube holding strip so that the tube or wire is held in a predetermined place but is yieldably movable in response to manipulation of the surgical instrument so as not to restrain movement of the instrument; and an attachment strip having an adhesive coating on one side for attaching it to a surgical instrument and a surface of interlacing material on the other side for engagement with said intertwining surface of said pad to provide a nesting place for the instrument when not in use.

7. A device, as claimed in claim 6, further including:
a first eyelet in said pad; and a second eyelet in said tube holding one end of said strip, said one end of said connecting strap being connected to said first eyelet and said other end of said strap being connected to said second eyelet.

8. A device as claimed in claim 7, wherein: said first eyelet is adjacent the edge of said pad.

9. A device, as claimed in claim 7, wherein: said second eyelet attaches said tab to said strip.

10. A device as claimed in claim 6, wherein: said strap is a rubber band.

* * * * *